(12) United States Patent
Lindroos et al.

(10) Patent No.: US 9,677,810 B2
(45) Date of Patent: Jun. 13, 2017

(54) METHOD FOR IMPROVING QUALITY AND FUNCTIONALITY OF FILTER PAPER SUITABLE FOR COLLECTING BIOLOGICAL SAMPLES

(75) Inventors: Hanne Marika Lindroos, Turku (FI); Outi Maria Lehtinen, Rusko (FI); Pekka Tapani Mattsson, Turku (FI); Elina Maaret Tuomola, Littoinen (FI)

(73) Assignee: WALLAC OY, Turku (FI)

( * ) Notice: Subject to any disclaimer, the term of this patent is extended or adjusted under 35 U.S.C. 154(b) by 629 days.

(21) Appl. No.: 13/985,619

(22) PCT Filed: Feb. 2, 2012

(86) PCT No.: PCT/FI2012/050093
§ 371 (c)(1),
(2), (4) Date: Sep. 19, 2013

(87) PCT Pub. No.: WO2012/110693
PCT Pub. Date: Aug. 23, 2012

(65) Prior Publication Data
US 2014/0000124 A1    Jan. 2, 2014

Related U.S. Application Data

(60) Provisional application No. 61/444,272, filed on Feb. 18, 2011.

(30) Foreign Application Priority Data

Feb. 18, 2011 (FI) .................................. 20115157

(51) Int. Cl.
| | |
|---|---|
| *G01N 31/00* | (2006.01) |
| *G01N 33/53* | (2006.01) |
| *F26B 1/00* | (2006.01) |
| *G01N 1/28* | (2006.01) |
| *G01N 33/52* | (2006.01) |

(52) U.S. Cl.
CPC ................. *F26B 1/00* (2013.01); *G01N 1/28* (2013.01); *G01N 33/521* (2013.01); *G01N 2001/2826* (2013.01)

(58) Field of Classification Search
CPC ........ A01N 25/30; A01N 31/02; A01N 35/02; A01N 37/02; A01N 2300/00; A61K 27/54; A61K 31/00; A61K 45/06
See application file for complete search history.

(56) References Cited

U.S. PATENT DOCUMENTS

| | | | |
|---|---|---|---|
| 3,802,842 A | 4/1974 | Lange et al. | |
| 7,682,009 B1 | 3/2010 | Sliwa, Jr. et al. | |
| 2002/0150761 A1* | 10/2002 | Lange ..................... A61L 15/28 428/407 |
| 2003/0113906 A1 | 6/2003 | Sangha et al. | |

FOREIGN PATENT DOCUMENTS

WO    85/04424    10/1985

OTHER PUBLICATIONS

International Search Report dated May 11, 2012 in corresponding PCT application.

* cited by examiner

*Primary Examiner* — Lisa Cook
(74) *Attorney, Agent, or Firm* — Young & Thompson

(57) ABSTRACT

A method for diminishing variation between and/or within individual sheets of filter papers which are suitable for collecting samples of biological material, e.g. blood, is described. The method includes at least one of the following: subjecting the sheets of filter paper to gaseous substance containing at least 30 grams water per cubic meter and/or wetting the sheets of filter paper with water and subsequently drying the sheets of filter paper. According to tests, the above-described treatment significantly reduces the undesirable variation between results analyzed from sheets of filter paper and impregnated with same biological material for test purposes.

7 Claims, 5 Drawing Sheets

```
              START
                │
                ▼
┌───────────────────────────────────┐
│ Subject a sheet of filter paper   │ ─── 301
│ to gaseous substance containing   │
│ at least 30 grams water per       │
│ cubic meter.                      │
└───────────────────────────────────┘
                │
                ▼
┌───────────────────────────────────┐
│ Impregnate at least one sample of │ ─── 304
│ biological material into the      │
│ sheet of filter paper.            │
└───────────────────────────────────┘
                │
                ▼
              END
```

Figure 3a

```
          ┌─────────┐
          │  START  │
          └────┬────┘
               ▼
┌──────────────────────────────────┐
│ Wet a sheet of filter paper with water. │──── 302
└──────────────┬───────────────────┘
               ▼
┌──────────────────────────────────┐
│ Dry the sheet of filter paper.   │──── 303
└──────────────┬───────────────────┘
               ▼
┌──────────────────────────────────┐
│ Impregnate at least one sample of │──── 304
│ biological material into the sheet of filter paper. │
└──────────────┬───────────────────┘
               ▼
          ┌─────────┐
          │   END   │
          └─────────┘
```

Figure 3b

METHOD FOR IMPROVING QUALITY AND FUNCTIONALITY OF FILTER PAPER SUITABLE FOR COLLECTING BIOLOGICAL SAMPLES

FIELD OF THE INVENTION

The invention relates to a method for improving properties of filter paper suitable for collecting samples of biological material, e.g. blood. More particularly, the invention relates to a method for diminishing variation of properties between and/or within individual sheets of filter paper. Furthermore, the invention relates to a method for handling biological material with the aid of filter paper. Furthermore, the invention relates to a method for diminishing variation between results to be analyzed from sheets of filter paper each being impregnated with at least one sample of biological material.

BACKGROUND

A conventional practice is to impregnate one or more sample drops of biological material to be examined into a sheet of filter paper, dry the sheet of filter paper impregnated with the biological material, and then send the sheet of filter paper to a laboratory for examination. The biological material to be examined can be, for example, blood of a newborn baby. In the laboratory, one or more sample disks containing the biological material to be examined are cut or punched out from the sheet of filter paper and then the one or more sample disks that have been cut or punched are subjected to analysis. It has, however, turned out that properties of the filter paper may vary between filter papers. In some cases, these property variations may result in variation between measurement results obtained from sheets of filter paper impregnated with same biological material. FIG. 1 shows a histogram of results measured in an example case in which blood was impregnated into seven different sheets of filter paper from different filter paper batches. The analyte was measured by eluting the blood from the sample disk punched out from the filter paper impregnated with blood and by assaying the analyte. The results were obtained by measuring fluorescence. The vertical axis of the histogram shown in FIG. 1 is the count number obtained with the photo detector. The count number is inversely proportional to the activity of analyte. In this example case, the analyte that is measured is biotinidase which is an enzyme that catalyses the cleavage of biotin, vitamin H, from small biotinylated peptides and biocytin, thus, recycling the vitamin. The reaction is hydrolytic, in which the substrate, i.e. the molecules at the beginning of the reaction, is converted to the products of the reaction. For example, biocytin can be converted to biotin and lysine. Biotinidase can also catalyze the cleavage of synthetic substrates that release a fluorescent dye, such as biotin-6-aminoquinoline, for screening of newborns for biotinidase deficiency. Enzyme activity is defined as the moles of substrate converted per unit time. Enzyme activity is a measure of the quantity of active enzyme present and is hence dependent on conditions, which should be specified. The SI unit is the katal, 1 katal=1 mol s$^{-1}$. A more practical and commonly used value is enzyme unit, 1 (U)=1 µmol min$^{-1}$. 1 U corresponds to 16.67 nanokatals. As can be seen from FIG. 1, there is, in this exemplifying case, relatively strong variation between results obtained with the different sheets S1-S7 of filter paper.

An inconvenience related to the above described phenomenon is that it may cause additional work and additional requirements to personnel collecting the samples of biological material, to personnel performing the measurements in laboratories, and also to specialists interpreting the analysis results.

SUMMARY

The following presents a simplified summary in order to provide a basic understanding of some aspects of various invention embodiments. The summary is not an extensive overview of the invention. It is neither intended to identify key or critical elements of the invention nor to delineate the scope of the invention. The following summary merely presents some concepts of the invention in a simplified form as a prelude to a more detailed description of exemplifying embodiments of the invention.

In accordance with the first aspect of the invention, there is provided a new method for diminishing variation between and/or within individual sheets of filter paper which are suitable for collecting samples of biological material. The method comprises:
  subjecting each sheet of filter paper to gaseous substance containing at least 30 grams water per cubic meter, and/or
  wetting, e.g. by immersing or rinsing, each sheet of filter paper with water and subsequently drying the sheet of filter paper.

In accordance with the second aspect of the invention, there is provided a new method for handling biological material with the aid of filter paper. The method comprises:
  treating a sheet of filter paper in at least one of the following ways (i, ii): (i) subjecting the sheet of filter paper to gaseous substance containing at least 30 grams water per cubic meter, and/or (ii) wetting the sheet of filter paper with water and subsequently drying the sheet of filter paper, and subsequently
  impregnating at least one sample of the biological material into the sheet of filter paper.

In accordance with the third aspect of the invention, there is provided a new method for diminishing variation between results to be analyzed from sheets of filter paper each being impregnated with at least one sample of biological material. The method comprises treating each sheet of filter paper in at least one of the following ways (i, ii) prior to impregnating the at least one sample of the biological material into that filter paper:
  (i) subjecting the filter paper to gaseous substance containing at least 30 grams water per cubic meter, and/or
  (ii) wetting the filter paper with water and subsequently drying the filter paper.

The fact that the quality and properties of filter paper can be improved in the above-described ways has significance at least for the following groups: the producers of analytical methods, the manufacturers of filter paper, the manufacturers of measurement and analysis devices, personnel collecting samples, personnel performing laboratory analysis, and specialists interpreting the analysis results.

A number of exemplifying, i.e. non-limiting, embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verbs "to comprise" and "to include" are used in this document as open limitations that neither exclude nor require the existence of unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which:

FIGS. 3a and 3b show flow charts of methods according to exemplifying embodiments of the invention for handling biological material with the aid of filter paper, FIG. 4 shows also the histogram of the results shown in FIG. 1.

FIG. 1 was already explained in conjunction with the description of the related prior art in the "Background"-section of this document.

DESCRIPTION OF THE EMBODIMENTS

Figure 2A:
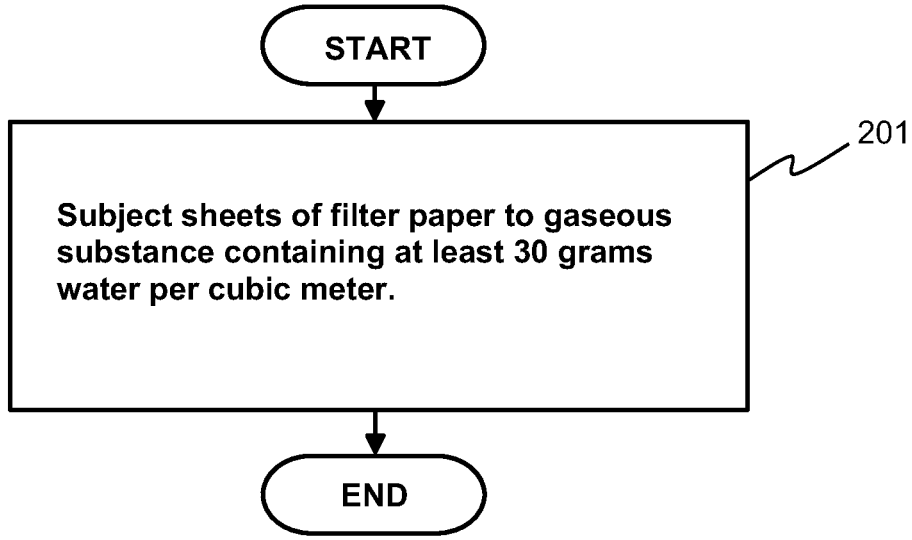
FIGS. 2a and 2b show flow charts of methods according to exemplifying embodiments of the invention for diminishing variation between and/or within individual sheets of filter paper which are suitable for collecting samples of biological material.

FIG. 2a shows a flow chart of a method according to an exemplifying embodiment of the invention for diminishing variation between and/or within individual sheets of filter paper which are suitable for collecting samples of biological material. The method comprises subjecting, in phase 201, the sheets of filter paper to gaseous substance containing at least 30 grams water per cubic meter. More preferably, the gaseous substance contains at least 40 grams water per cubic meter, and yet more preferably, the gaseous substance contains at least 50 grams water per cubic meter, and still more preferably, the gaseous substance contains at least 70 grams water per cubic meter. The gaseous substance can be, for example, moist air in which there is at least 30 grams water per cubic meter.

In a method according to an exemplifying embodiment of the invention, the sheets of filter paper are subjected to steam having temperature at least 100° C., or more advantageously at least 120° C. The sheets of filter paper may be subjected to the steam for a time period of e.g. at least 15 minutes.

Figure 2B:
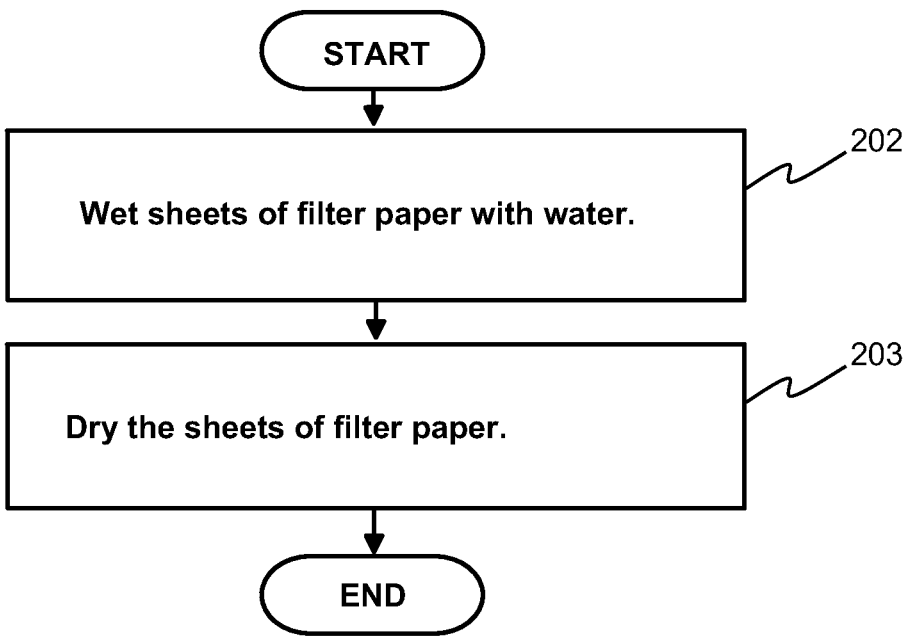

FIG. 2b shows a flow chart of a method according to another exemplifying embodiment of the invention for diminishing variation between and/or within individual sheets of filter paper which are suitable for collecting samples of biological material. The method comprises wetting, in phase 202, the sheets of filter paper with water and subsequently, in phase 203, drying the sheets of filter paper.

FIG. 3a shows a flow chart of a method according to an exemplifying embodiment of the invention for handling biological material with the aid of filter paper. The method comprises subjecting, in phase 301, a sheet of filter paper to gaseous substance containing at least 30 grams water per cubic meter, and subsequently in phase 304, impregnating at least one sample of the biological material into the sheet of filter paper. The biological material can be, for example, blood.

FIG. 3b shows a flow chart of a method according to another exemplifying embodiment of the invention for handling biological material with the aid of filter paper. The method comprises, in successive phases 302 and 303, wetting a sheet of filter paper with water and drying the sheet of filter paper, and subsequently in phase 304, impregnating at least one sample of the biological material into the sheet of filter paper.

A method according to an exemplifying embodiment of the invention further comprises measuring an analyte quantitatively and/or qualitatively from the biological material, e.g. blood, impregnated into the sheet of filter paper.

In a method according to an exemplifying embodiment of the invention, activity and/or concentration of the analyte is measured from the biological material, e.g. blood, impregnated into the sheet of filter paper.

In a method according to an exemplifying embodiment of the invention, the measuring of the analyte from the biological material, e.g. blood impregnated into the sheet of filter paper, is carried out as a fluorescence measurement. It should be, however, noted that methods according to various embodiments of the present invention are applicable also with various other measuring methods such as, for example, absorbance, time resolved fluorescence, luminescence, mass analysis.

A method according to an exemplifying embodiment of the invention comprises measuring activity of the biotinidase enzyme from blood impregnated into the sheet of filter paper.

Figure 1:
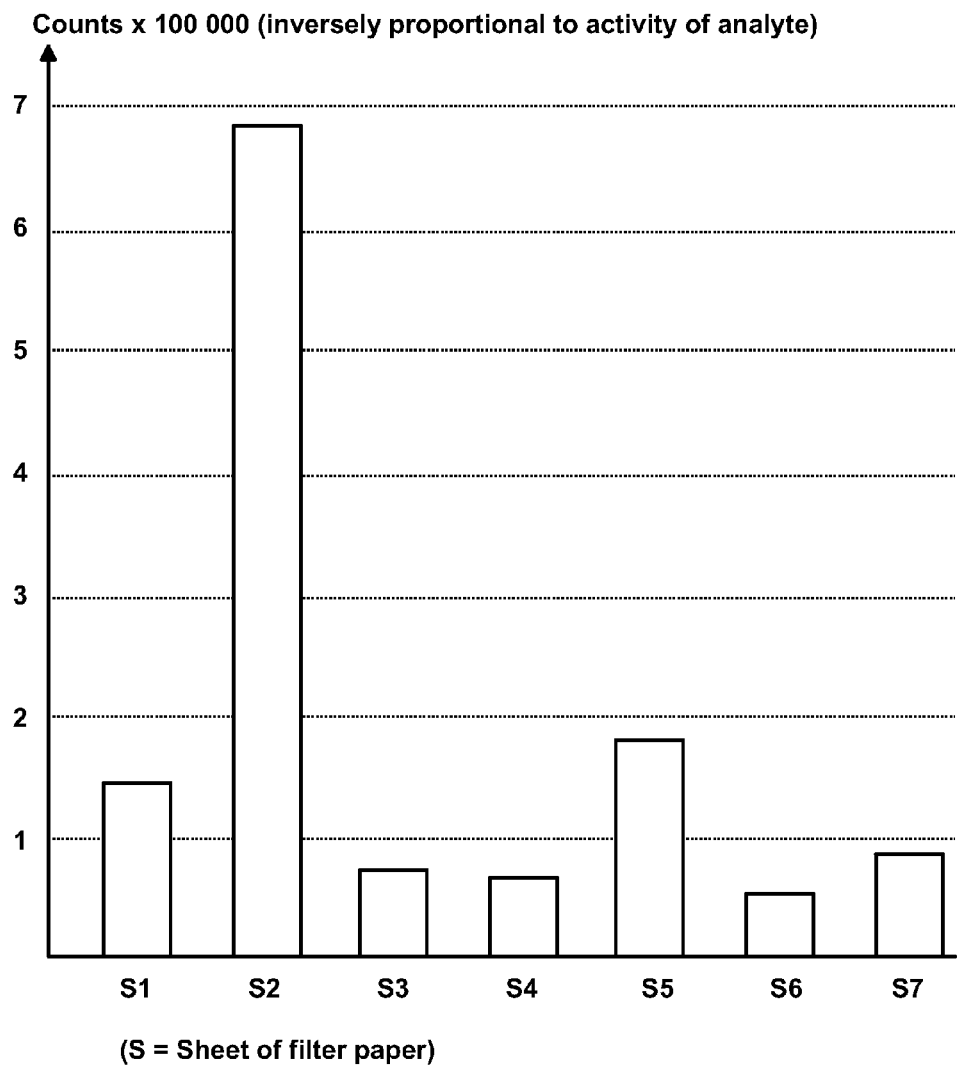
FIG. 1 shows a histogram of results measured in an example case in which blood was impregnated into seven different sheets of filter paper from different filter paper batches.
Figure 4:
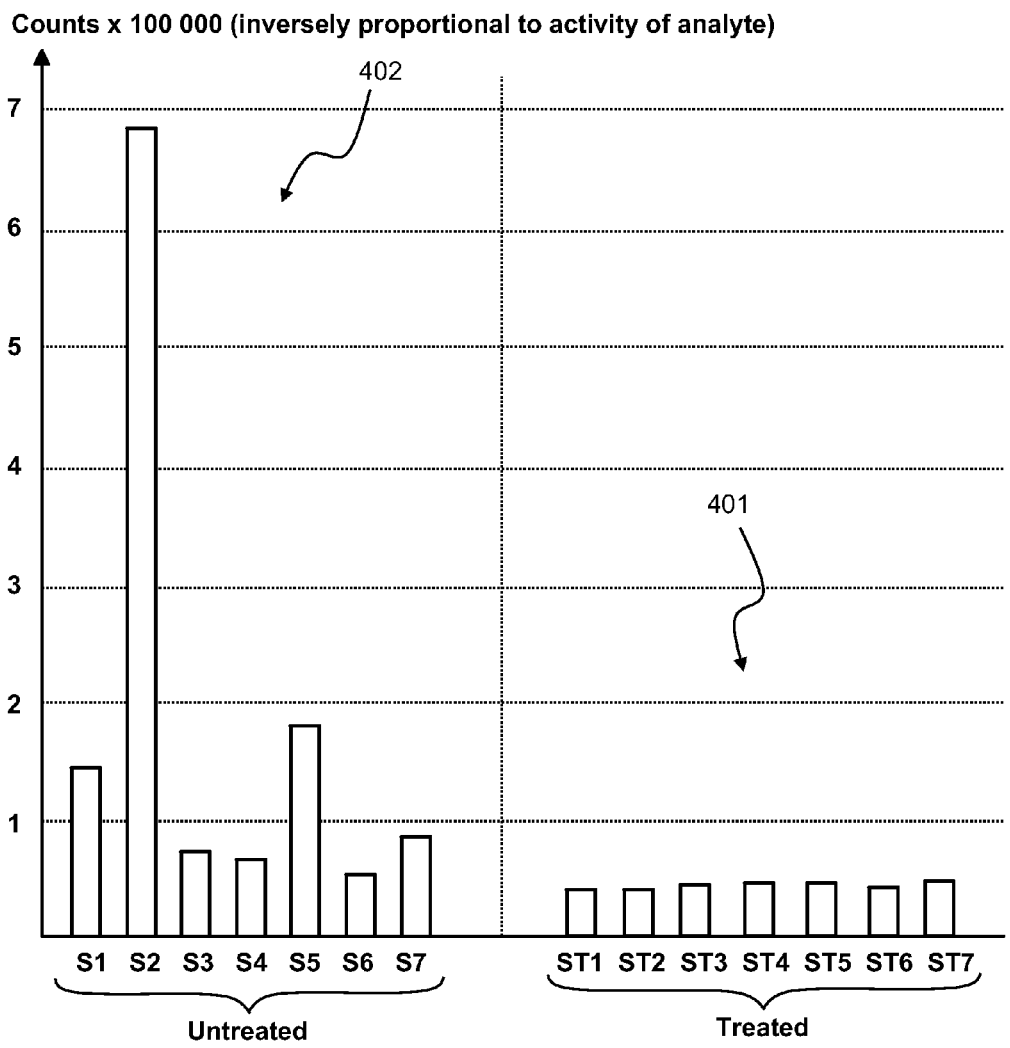
FIG. 4 shows a histogram of results measured in an example case in which blood was impregnated into seven different sheets of filter paper taken from the same filter paper batches as in the example case of FIG. 1 and furthermore treated with a method according to an exemplifying embodiment of the invention; for the purpose of comparison.

FIG. 4 shows a histogram 401 of results measured in an example case in which blood was impregnated into seven different sheets ST1-ST7 of filter paper that had been treated with a method according to an exemplifying embodiment of the invention. In this exemplifying case, the treatment was autoclavation, i.e. subjection the sheets ST1-ST7 of filter paper to high pressure saturated steam at 120° C. or more for a time period of typically 15-20 minutes. The sheets ST1-ST7 of filter paper have been taken from the same filter paper batches as the untreated sheets S1-S7 of filter paper used in the example case illustrated in FIG. 1. For the purpose of comparison, FIG. 4 shows also the histogram 402 of results that are shown in FIG. 1 and that relate to the corresponding untreated sheets S1-S7 of filter paper. The vertical axis of the histograms 401 and 402 shown in FIG. 4 is the count number obtained with a photo detector. The count number is inversely proportional to the activity of the analyte that is measured. In this example case, the analyte that is measured is biotinidase.

The specific examples provided in the description given above should not be construed as limiting. Therefore, the invention is not limited merely to the exemplifying embodiments described above.

What is claimed is:

1. A method for treating filter paper, the method comprising:
    subjecting sheets of the filter paper to a gaseous substance containing at least 30 grams water per cubic meter, and/or
    wetting the sheets of filter paper with water and subsequently drying the sheet of filter paper,
    wherein variation between the sheets of the filter paper is diminished,
the filter paper is configured for collecting samples of biological material by impregnation for a purpose of measuring analytes quantitatively and/or qualitatively from the biological material, and
a count number ×100,000 obtained with a photo detector, which is inversely proportional to an activity of the analyte being measured, is less than 1.

2. The method according to claim 1, wherein the gaseous substance is moist air in which there is at least 30 grams water per cubic meter.

3. The method according to claim 1, wherein the sheets of filter paper are subjected to steam having temperature at least 100° C.

4. The method according claim 3, wherein the temperature of the steam is at least 120° C.

5. The method according to claim 3, wherein the sheets of filter paper are subjected to the steam for a time period of at least 15 minutes.

6. The method according to claim 4, wherein the sheets of filter paper are subjected to the steam for a time period of at least 15 minutes.

7. The method according to claim 1, wherein the biological material is blood.

* * * * *